US012053777B2

(12) United States Patent
Hung et al.

(10) Patent No.: US 12,053,777 B2
(45) Date of Patent: Aug. 6, 2024

(54) DEVICES AND METHODS FOR DETECTING CANCEROUS CELLS

(71) Applicants: Academia Sinica, Taipei (TW); National Tsing Hua University, Hsinchu (TW)

(72) Inventors: Shang-Cheng Hung, Taipei (TW); Yen-Chun Ko, Taipei (TW); Cheng-Fang Tsai, Taipei (TW); Gwo-Bin Lee, Hsinchu (TW); Wei-Chun Tsai, Hsinchu (TW)

(73) Assignees: Academia Sinica, Taipei (TW); National Tsing Hua University, Hsinchu (TW)

( * ) Notice: Subject to any disclaimer, the term of this patent is extended or adjusted under 35 U.S.C. 154(b) by 1010 days.

(21) Appl. No.: 16/968,604

(22) PCT Filed: Feb. 27, 2019

(86) PCT No.: PCT/US2019/019712
§ 371 (c)(1),
(2) Date: Aug. 10, 2020

(87) PCT Pub. No.: WO2019/168890
PCT Pub. Date: Sep. 6, 2019

(65) Prior Publication Data
US 2021/0046479 A1   Feb. 18, 2021

(51) Int. Cl.
*B01L 3/00*  (2006.01)
*G01N 33/543*  (2006.01)
*G01N 33/574*  (2006.01)

(52) U.S. Cl.
CPC .. *B01L 3/502761* (2013.01); *G01N 33/54326* (2013.01); *G01N 33/57407* (2013.01);
(Continued)

(58) Field of Classification Search
CPC ....... B01L 3/502753; B01L 2200/0668; B01L 2300/0645; B01L 2300/0806;
(Continued)

(56) References Cited

U.S. PATENT DOCUMENTS

2013/0116423 A1\* 5/2013 Campbell ........... C08B 37/0063
536/55.1
2013/0157303 A1\* 6/2013 Fukunishi ........... C08B 37/0003
530/389.1

FOREIGN PATENT DOCUMENTS

WO    WO-2007092713 A2 \*  8/2007  ........ B01L 3/502761

OTHER PUBLICATIONS

W. C. Tsai, et al., "A microfluidic system for detection of cholangiocarcinoma cells by using heparan sulfate octasaccharides," 2017 IEEE 12th International Conference on Nano/Micro Engineered and Molecular Systems (NEMS), Los Angeles, CA, US (Year: 2017).\*
(Continued)

*Primary Examiner* — P. Kathryn Wright
*Assistant Examiner* — Curtis A Thompson
(74) *Attorney, Agent, or Firm* — NZ CARR LAW OFFICE

(57) ABSTRACT

Disclosed herein is an integrated microfluidic chip for detecting cancerous cells, particularly, cholangio-cancerous cells, from a biological sample. Also disclosed herein is a method of detecting cholangio-cancerous cells from a biological sample.

4 Claims, 2 Drawing Sheets

(52) U.S. Cl.
CPC .............. *G01N 33/57488* (2013.01); *B01L 2200/0668* (2013.01); *B01L 2200/10* (2013.01); *B01L 2200/16* (2013.01); *B01L 2400/043* (2013.01); *G01N 2400/12* (2013.01); *G01N 2446/20* (2013.01)

(58) Field of Classification Search
CPC ....... B01L 2300/161; B01L 2300/0861; G01N 2001/4083; G01N 2035/00495; G01N 35/00069; G01N 1/4077; C12Q 1/18
See application file for complete search history.

(56) References Cited

OTHER PUBLICATIONS

Bülow, H et al.. "The molecular diversity of glycosaminoglycans shapes animal development." Annual review of cell and developmental biology vol. 22 (2006): 375-407. (Year: 2006).*

Weiss, R et al. "Small molecule antagonists of cell-surface heparan sulfate and heparin-protein interactions." Chemical science vol. 6,10 (2015): 5984-5993 (Year: 2015).*

* cited by examiner (a)

(b)

DEVICES AND METHODS FOR DETECTING CANCEROUS CELLS

CROSS-REFERENCE TO RELATED APPLICATIONS

This application claims priority under 35 U.S.C. § 119(e) to U.S. Provisional application, U.S. Ser. No. 62/636,910, filed Mar. 1, 2018, which is incorporated by reference herein in its entirety.

STATEMENT REGARDING PRIOR DISCLOSURES BY THE INVENTOR OR A JOINT INVENTOR UNDER 37 C.F.R. 1.77(B)(6)

Part of the subject matter of the invention described in the present application was published by the inventors, Wei-Chun Tsai and Gwo-Bin Lee in an article titled "A Microfluidic System for Detection of Cholangiocarinoma Cells by Using Heparan Sulfate Octasaccharides." The article was published during Apr. 9 to Apr. 12, 2017 in IEEE 12$^{th}$ International Conference held in Los Angeles, CA (USA). The publication was made by and/or originated from 2 members of the inventive entity of the present invention, and the entirety of this article is incorporated herein by reference. A copy of the article is provided in a concurrently filed Information Disclosure Statement pursuant to the guidance of 78 Fed. Reg. 11076 (Feb. 14, 2013)."

BACKGROUND OF THE INVENTION

1. Field of the Invention

The present disclosure in general relates to devices and methods for the detection of cancerous cells from a biological sample.

2. Description of Related Art

Cholangiocarcinoma (CCA) is a kind of primary malignant liver cancer occurring at the bile ducts which drain bile juice from the liver into the small intestine. It exhibits relatively poor prognosis with a five-year survival rate less than 10% after diagnosed. Nowadays, imaging techniques, including ultrasonography, magnetic resonance imaging and computed tomography, and pathological diagnoses by forceps biopsy or brush cytology are the main tools applied to detect CCA. These methods are limited by tumor sizes, localization and lesions so that they are unable to discover CCA tumor at the early stage. The most common tumor biomarkers used to diagnose CCA are carbohydrate antigen 19-9 (CA19-9) and carcinoembryonic antigen (CEA). However, the sensitivity and specificity of CA19-9 and CEA are still not satisfactory in clinical applications.

Therefore, three exists in the related art a need of new biomarkers for detection CCA at an early stage that would render early diagnose and treatment of CCA.

SUMMARY OF THE INVENTION

Inventors of the present invention unexpectedly identify some novel sulfated octasaccharides are useful as biomarkers that bind to the surface of cholangio-cancerous cells, thus they are useful for making prognosis on whether a subject is at risk of developing cholangiocarcinoma. Accordingly, the present disclosure provides an integrated microfluidic chip for analyzing a biological sample, as well as a method for making prognosis on whether a subject has or is at risk of having a cholangiocarcinoma based on the analysis generated from the integrated microfluidic chip.

Accordingly, the first aspect of the present disclosure is directed to the novel use of a sulfated octasaccharide, which acts as a biomarker for the identification of cholangio-cancerous cells from a biological sample. The sulfated octasaccharide has the structure of formula (I),

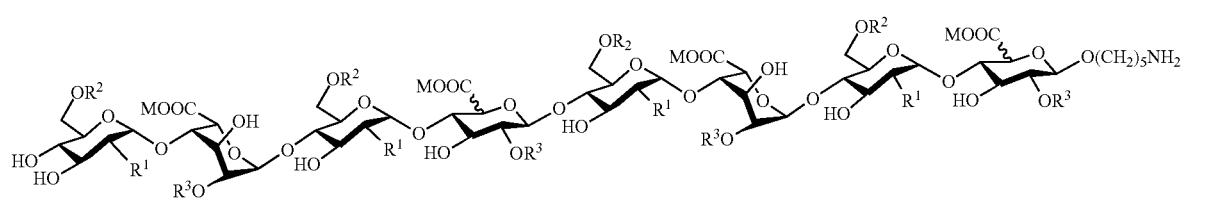

(I)

Wherein $R^1$ is —NHAc or —NHSO$_3$M; $R^2$ and $R^3$ are independently H, or —SO$_3$M; and M is a monovalent cation selected from the group consisting of sodium ion, potassium ion, lithium ion and ammonium ion.

According to one preferred embodiment of the present disclosure, in the formula (I), $R^1$ is —NHSO$_3$Na; and $R^2$ and $R^3$ are independently —SO$_3$Na.

According to another preferred embodiment of the present disclosure, in the formula (I), $R^1$ is —NHSO$_3$Na, $R^2$ and $R^3$ are independently H.

The second aspect of the present disclosure is directed to a method of detecting cholangio-cancerous cells from a biological sample. The method includes the step of contacting the biological sample with a magnetic bead pre-coated with the sulfated octasaccharide of formula (I) described above or its pharmaceutically acceptable salt thereof, in which a binding between the magnetic bead and the biological sample indicates the presence of cholangio-cancerous cells in the biological sample.

According to embodiments of the present disclosure, the sulfated octasaccharide of formula (I) is further coupled to a biotin.

According to preferred embodiments of the present disclosure, the magnetic bead pre-coated with the sulfated octasaccharide of formula (I), in which $R^1$ is —NHSO$_3$Na, $R^2$ and $R^3$ are independently H.

According to other embodiments of the present disclosure, the magnetic bead pre-coated with the sulfated octasaccharide of formula (I), in which $R^1$ is —NHSO$_3$Na; and $R^2$ and $R^3$ are independently —SO$_3$Na.

According to embodiments of the present disclosure, the biological sample may be selected from the group consisting of blood, plasma, serum, urine, sputum, saliva, tissue sample, biopsy, and tissue lysate.

The third aspect of the present disclosure is directed to a microfluidic chip for analyzing a biological sample, such as determining whether the biological sample is cancerous. The microfluidic chip comprises:

a plurality of wash buffer chambers configured to hold a wash buffer therein;

a plurality of capture chambers respectively configured to capture a cancerous cell on a magnetic bead pre-coated with a biomarker of the cancerous cell;

a waste chamber configured to hold the uncaptured cancerous cell washed out from the plurality of capture chambers; and a plurality of microchannels connecting the wash buffer chamber, the plurality of capture chambers and the waste chamber.

According to embodiments of the present disclosure, the microfluidic chip is fabricated on a glass substrate and at least one layer of polydimethylsiloxane.

According to one preferred embodiment of the present disclosure, the microfluidic chip comprises in its structure, six wash buffer chambers, six capture chambers and one waste chamber, respectively coupled to each other and connected by the microchannels.

According to embodiments of the present disclosure, each of the capture chambers is configured to isolate the magnetic bead with bound cancerous cell from a fluid sample.

According to embodiments of the present disclosure, the magnetic bead is pre-coated with a sulfated octasaccharide of formula (I), $$\text{(I)}$$

wherein, $R^1$ is —NHAc or —NHSO$_3$M; $R^2$ and $R^3$ are independently H, or —SO$_3$M; and M is a monovalent cation selected from the group consisting of sodium ion, potassium ion, lithium ion and ammonium ion.

According to embodiments of the present disclosure, the sulfated octasaccharide of formula (I) is further coupled to a biotin.

According to embodiments of the present disclosure, in the sulfated octasaccharide of formula (I), $R^1$ is —NHSO$_3$Na; and $R^2$ and $R^3$ are independently —SO$_3$Na.

According to embodiments of the present disclosure, in the sulfated octasaccharide of formula (I), $R^1$ is —NHSO$_3$Na, $R^2$ and $R^3$ are independently H.

The fourth aspect of the present disclosure is directed to a kit for analyzing a biological sample. The kit includes, the microfluidic chip of the present disclosure, magnetic beads pre-coated with a biomarker, at least one reagents for analyzing a biological sample using the microfluidic chip of the present disclosure; and a legend providing instruction to a user on how to use the kit.

According to one embodiment of the present disclosure, the biomarker is the sulfated octasaccharide of formula (I) described above, where $R^1$ is —NHSO$_3$Na; and $R^2$ and $R^3$ are independently —SO$_3$Na.

According to another embodiment of the present disclosure, the biomarker is the sulfated octasaccharide of formula (I) described above, where $R^1$ is —NHSO$_3$Na, $R^2$ and $R^3$ are independently H.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute apart of the specification, illustrate various example systems, methods and other exemplified embodiments of various aspects of the invention. The present description will be better understood from the following detailed description read in light of the accompanying drawings, where.

DETAILED DESCRIPTION OF THE PREFERRED EMBODIMENTS

Figure 1:
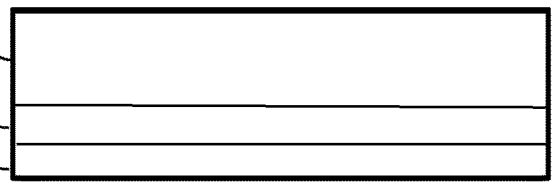
FIG. 1: Schematic drawings of a microfluidic chip. (a) A schematic view of the microfluidic chip, which includes from bottom to top, a glass substrate, a thin PDMS layer, and a thick PDMS layer; and (b) a schematic illustration of wash buffer chambers, capture chambers, waster chamber and microchannels engraved on a PDMS layer.
Figure 1:
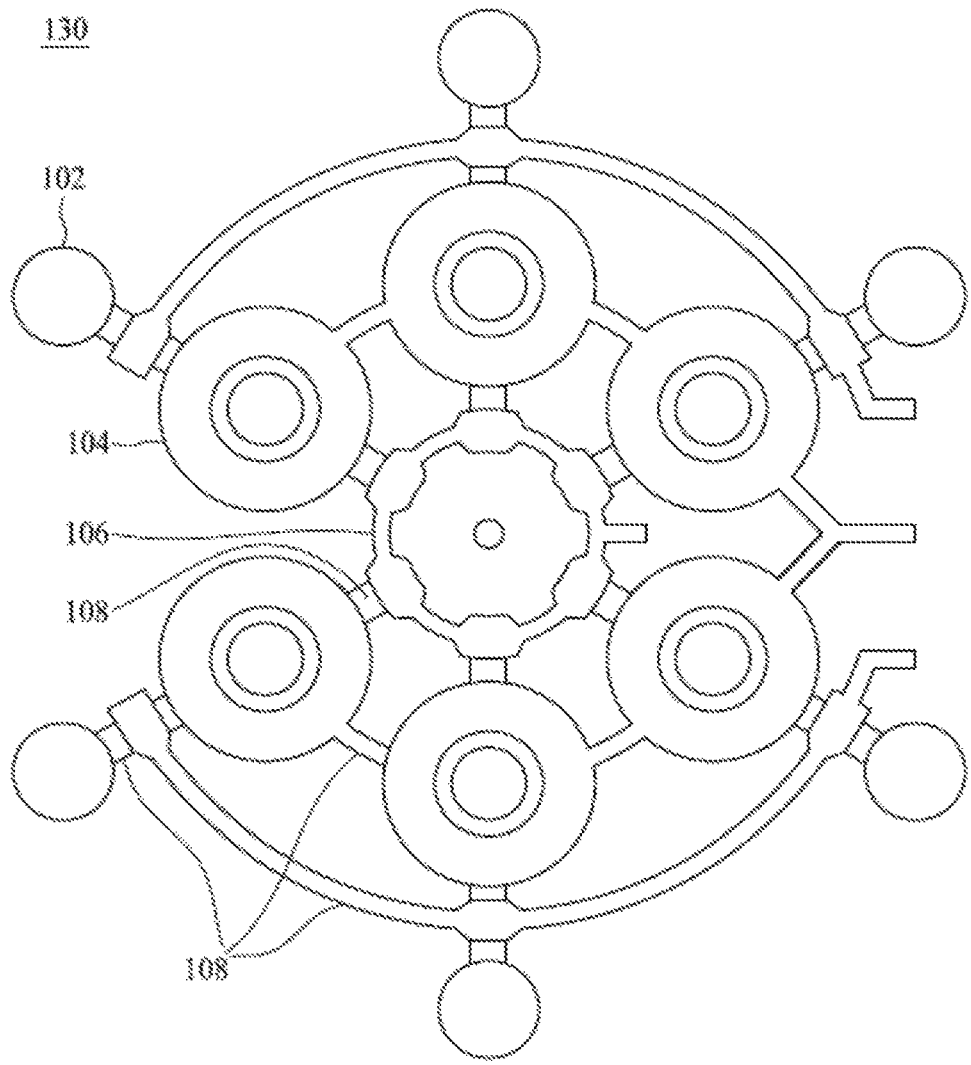

The detailed description provided below in connection with the appended drawings is intended as a description of the present disclosure and is not intended to represent the only forms in which the present disclosure may be constructed or utilized.

1. Definitions

Unless otherwise indicated, the term "patient" or "subject" may be used interchangeably in the present disclosure, and refers to any animal. The animal can be a human subject, or a non-human subject. The subject may be a human, but can also be a mammal in need of veterinary treatment, e.g., domestic animals or game animals, farm animals, and laboratory animals (e.g., rats, mice, guinea pigs, primates, and the like). Usually the animal is a non-human mammal, such as a non-human primate. Non-human primates include chimpanzees, cynomologous monkeys, spider monkeys, and macaques, e.g., Rhesus or Pan. Domestic animals and game animals include cows, horses, pigs, sheep, deer, bison, buffalo, mink, felines (e.g., domestic cats, canines (e.g., dogs)), wolf and fox, avian species (e.g., chicken, turkey, and ostrich), and fish (e.g., trout, catfish, and salmon).

The term "contacting" is used herein with respect to a cell (e.g., a cell in a biological sample) and refers to any mode of delivery or "administration" of an agent either to cells or the biological sample, in which the agent (e.g., a sulfated octasaccharide of the present disclosure or a magnet bead pre-coated with the sulfated octasaccharide of the present disclosure) is brought into contact with one or more cells in sufficient amount to achieve affinity binding therebetween.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. The Sulfated Octassacharides of the Present Invention

Aspects of the present disclosure relate to the findings that certain sulfated octasaccharides are useful as biomarkers in methods and/or kits for the identification and/or detection of cancerous cells in a biological sample. Examples of the sulfated octasaccharides are described herein.

In one aspect, the present invention relates to a sulfated octasaccharide of formula (I):

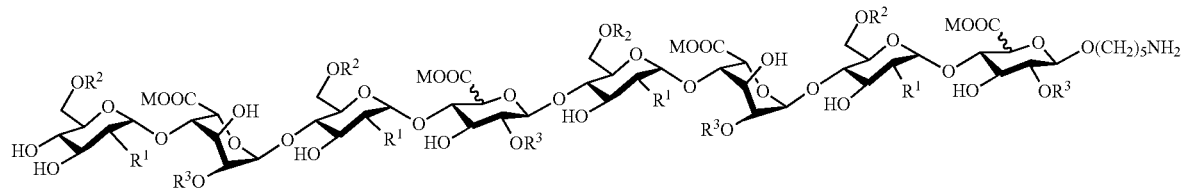

(I)

wherein $R^1$ is —NHAc or —NHSO$_3$M; $R^2$ and $R^3$ are independently H, or —SO$_3$M; and M is a monovalent cation selected from the group consisting of sodium ion, potassium ion, lithium ion and ammonium ion.

In some embodiments of the present disclosure, $R^1$ is —NHSO$_3$Na; and $R^2$ and $R^3$ are independently —SO$_3$Na.

In further embodiments of the present disclosure, $R^1$ is —NHSO$_3$Na, $R^2$ and $R^3$ are independently H.

The sulfated octasaccharides of the present disclosure may be prepared in accordance with procedures described in the working examples. All stereoisomers of the present compounds, such as those which may exist due to asymmetric carbons on the R substituents of the compound of formula (I) including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

3. Method of Use

The sulfated octasaccharide of formula (I) may bind to surfaces of cancerous cells, particularly cancers originated from cholangio bile duct. Accordingly, the present disclosure thus encompasses a method of identifying or detecting cholangio-cancerous cells from a biological sample.

The present method includes contacting a biological sample of a subject with a magnetic bead pre-coated with the sulfated octasaccharide of formula (I), in which a binding between the magnetic bead and the biological sample indicates the presence of cholangio-cancerous cells in the biological sample.

According to embodiments of the present disclosure, the sulfated octasaccharide of formula (I) pre-coated on the magnetic bead is further coupled to a biotin.

According to preferred embodiments of the present disclosure, in the sulfated octasaccharide of formula (I), $R^1$ is —NHSO$_3$Na, $R^2$ and $R^3$ are independently H.

According to other embodiments of the present disclosure, in the sulfated octasaccharide of formula (I), $R^1$ is —NHSO$_3$Na; and $R^2$ and $R^3$ are independently —SO$_3$Na.

Examples of the biological sample suitable for use in the present method includes but are not limited to, blood, plasma, serum, urine, sputum, saliva, tissue sample, biopsy, and tissue lysate. In one preferred embodiment, the biological sample is blood.

The present disclosure thus provides a method of making a prognosis on whether a subject has a cholangiocarcinoma. The prognosis is made to a sample of the subject, which may be any of the followings, blood, plasma, serum, urine, sputum, saliva, tissue sample, biopsy, and tissue lysate. The method comprises: incubating the tissue sample with magnetic beads pre-coated with the sulfated octasaccharide of formula (I) for a sufficient period of time, wherein, if binding was observed in the tissue sample and the magnetic beads pre-coated with the sulfated octasaccharide of formula (I), then the subject has a cholangiocarcinoma.

According to certain embodiments, the tissue sample may be blood, plasma, serum, urine, sputum, saliva, tissue sample, biopsy, and tissue lysate. In one preferred embodiment, the tissue sample is blood.

According to preferred embodiments of the present disclosure, the magnetic bead is pre-coated with the sulfated octasaccharide of formula (I), in which $R^1$ is —NHSO$_3$Na, $R^2$ and $R^3$ are independently H.

According to other embodiments of the present disclosure, the magnetic bead is precoated with the sulfated octasaccharide of formula (I), in which $R^1$ is —NHSO$_3$Na; and $R^2$ and $R^3$ are independently —SO$_3$Na.

4. Microfluidic Chip

In certain embodiments, the present disclosure relates to an integrated microfluidic chip, which expedites the detection and/or isolation of cancerous cells from a biological sample.

Reference is made to FIG. 1, which is a schematic drawing of a microfluidic chip 100 of the present disclosure, which is fabricated on a glass substrate and at least one layer of polydimethylsiloxane (PDMS). As depicted in FIG. 1(a), the microfluidic chip 100 comprises, from bottom to top, a glass substrate 110; a first PDMS layer 120, and a second PDMS layer 130, in which the first and second PDMS layers 120, 130 respectively serve as a liquid channel layer and an air channel layer. Preferably, the first PDMS layer 120 is relatively thinner than the second PDMS layer 130. Microstructures, such as fluid chambers and fluid conducts (or fluid channels) are constructed or engraved on the first and second PDMS layers 120, 130 via computer numerical control (CNC) machining process known in the art (e.g., EGX-400, Roland Inc., Japan).

FIG. 1(b) is a representative schematic drawing of the fluid chambers and/or fluid conducts constructed on the second PDMS layer 130. As depicted, six wash buffer chambers 102 (a to f), six capture chambers 104 (a to f), a waste chamber 106, and a plurality of microchannels 108 are constructed on the PDMS layer 130. For the sake of brevity, only one of the six wash buffer chambers, i.e., chamber 102 and one of the six capture chambers, i.e., chamber 104 are identified in FIG. 1(b). The chambers are arranged in circular manner, with the waste chamber 106 being disposed in the center of the PDMS layer, six capture chambers 104 (a to f) are engraved around the waste chamber 106, with each capture chambers being coupled to its neighboring capture chambers and the waste chamber via microchannels 108. Then, six wash buffer chambers 102 (a to f) are engraved around the six capture chambers 104 (a to f), with each wash buffer chambers being coupled to its neighboring wash buffer chambers and capture chambers via microchannels 108. By this arrangement, each wash buffer chambers 102 (a to f), capture chambers 104 (a to f) and waste chamber 106 are in fluid communication via microchannels 108. Chambers and microchannels may be constructed in the same manner on the first PDMS layer 120.

During operation, suitable amounts of a fluidic sample (e.g., blood or plasma) is first loaded into each capture chambers 104 (a to f). Then, magnetic beads pre-coated with biomarkers (i.e., the present sulfated octasaccharide of formula (I)) are added into each capture chambers 104 (a to f), and the mixture in each chambers 104 (a to f) is allowed to react for a sufficient period of time (e.g., at least 15 minutes) to allow the cancerous cells to bind to the biomarkers on the magnetic beads via affinity binding. Magnetic beads having desired cancerous cells bound thereon are then collected by a magnetic force, while unbounded cells as well as other components in the biological sample are then washed out via wash buffers loaded in the wash buffer chambers 102 (a to f) and collected in the waste chamber 106.

According to preferred embodiments of the present disclosure, the microfluidic chip is constructed to comprise six wash buffer chambers, and six capture chambers; accordingly, the microfluidic chip may be used to identify and/or capture desired cancerous cells under six different conditions, such as under the use of six types of magnetic beads respectively coated with a different type of biomarkers thereon, or under the use of one type of biomarkers but six different binding conditions (e.g., pH, ionic strength and etc). By such manner, the detection of cancerous cells in a fluidic sample is expedited, in which the detection is relatively more complete as a wider range of biomarkers and/or conditions may be employed.

In one preferred embodiment of the present disclosure, magnetic beads pre-coated with the present sulfated octasaccharide of formula (I) are respectively loaded into the capture chambers of the microfluidic chip, and cholangiocancerous cells are identified by magnetic beads pre-coated with sulfated octasaccharide HS1 and HS12.

Additionally and optionally, each magnetic beads is further coupled to a biotin to amplify the detection signal.

5. Kits

A further aspect of the present invention relates to a kit for the identification and/or detection of cancerous cells from a biological sample. The kit includes, at least, the microfluidic chip of the present disclosure; magnetic beads pre-coated with a biomarker, at least one reagents for analyzing a biological sample using the microfluidic chip, and a legend providing instruction to the user on how to use the kit.

According to preferred embodiments of the present disclosure, the kit includes at least three containers, and a legend providing instructions to a user on how to use the kit. The first container may house therein the microfluidic chip of the present disclosure. The second container may house therein magnetic beads pre-coated with the sulfated octasaccharide HS1, magnetic beads pre-coated with the sulfated octasaccharide HS12, or a mixture thereof. The third container may house therein buffer solutions necessary for performing the analysis, such as buffer solutions for washing out the magnetic beads unbound with cancerous cells. The legend may be in the form of a pamphlet, tape, CD, VCD or DVD.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods

Cell culture. HEK293T (from human embryonic kidney) and COS-1 (from monkey kidney) cells were cultured in Dulbecco's modified eagle's medium (DMEM) supplemented with heat-inactivated 10% fetal calf serum (FCS). Neuro2a cells (established from mouse neuroblastoma) were cultured in RPMI-1640 supplemented with 10% FCS.

SNU478, HuCCT1, Huh28, BxPC3, and HCT8 were respectively cultured in RPMI 1640 (Gibco®, Invitrogen Co., USA) containing 100 U/mL penicillin and 100 g/mL streptomycin (Pen Strep, Gibco®, Invitrogen Co., USA), 10% fetal bovine serum (FBS, Gibco®, Invitrogen Co., USA). KKU100, MMNK1, and HepG2 were espectively cultured in DMEM complemented with 100 U/mL penicillin, 100 g/mL streptomycin and 10% fetal bovine serum. All cells were cultured at 37° C. under an atmosphere containing 5% $CO_2$.

Preparation of magnetic beads pre-coated with a sulfated octasaccharide. The surface of magnetic beads was respectively coated with the sulfated octasaccharides of the present invention (e.g., HS1, HS12 and etc) with three different concentrations (1 µM, 10 µM and 100 µM). Briefly, sulfated octasaccharides were first incubated with Dynabeads® MyOne™ Streptavidin T1 (~7-10×10$^9$ beads/mL, Ø=1 µm, Invitrogen Co., USA) in a volume ratio of 1:10 for 30 min. Then beads were collected by using a magnet for 5 min, followed by discarding the supernatant and washing thrice by using 1-mL deionized (DI) water. Finally, the coated beads were suspended in the equal volume of DI water as the initial volume of Dynabeads® taken from the vial.

Construction of a microfluidic chip. In order to efficiently capture cancerous cells by using magnetic beads, an integrated microfluidic chip was constructed in accordance with the procedures described by Tsai W.-C. et al ("A Microfluidic System for Detection of Cholangiocarinoma Cells by Using Heparan Sulfate Octasaccharides." 2017 IEEE 12$^{th}$ International Conference, Los Angeles, Calif. USA). Briefly, the integrated microfluidic chip was manufactured with a two polydimethylsiloxane (PDMS) layers and a glass substrate. One of the two PDMS layers was thicker than the other PDMS layer. The thick PDMS layer was used for the air channel layer, and the thin PDMS layer served as the liquid channel layer, finally, a glass substrate was used to seal the PDMS layers.

The master molds of the air and liquid channel layers were engraved into microstructures on polymethylmethacrylate (PMMA) by using the computer-numerical-control (CNC) machining process (EGX-400, Roland Inc., Japan) with a 0.5-mm drill bit. Then, the PDMS casting and replica-molding processes were performed to obtain the inverse structures of master molds. The production of PDMS was performed by mixing the curing agent and the PDMS pre-polymer (Sylgard 184A/B, Sil-More Industrial Ltd., USA) in a ratio of 1:10 by weight, and removing all bubbles by placing it under a vacuum. After 40-min removing of the bubbles, the master molds were manually filled up with the PDMS mixture and cured at 70° C. for 2 hrs. Then, two cured PDMS layers were peeled off mechanically from the master molds, followed by bonding the thick and thin PDMS layers together by plasma oxidation. The assembled PDMS layers were finally bonded with the glass substrate by the same procedure of plasma oxidation, thereby forming the microfluidic chip.

Capturing Cancerous Cells Using the Microfluidic Chip

The microfluidic chip constructed above was employed to capture cancerous cells. Briefly, 2×10$^5$ cells from various types of cancerous cell lines were suspended in 100 µL×phosphate buffered saline (PBS) buffer and loaded into six capture chambers, respectively. 10 µL of different concentrations of sulfated octasaccharides coated beads were manually pipetted in the capture chambers, and gently mixed with cells by the micropumps for 15 min. After incubation, the cells were identified and bound by the magnetic beads pre-coated with the sulfated octasaccharides of formula (I) of the present invention. Then, these captured cells were collected with a magnetic force and washed by 1×PBS buffer. After isolating, the beads and captured cells were suspended in 100 µL 1×PBS buffer, and finally loaded into a hemocytometer to calculate the capture rates.

Statistical Analysis

No statistical method was used to predetermine sample size of experiments. Data were analyzed and are presented as mean with s.e.m. or s.d. (indicated in each figure legends). Data sets were analyzed using the Student's t-test to compare two populations. In the case of more than two groups, the One-way ANOVA combined with post hoc Duncan's or Tukey test to correct for multiple comparisons was applied. All tests were performed as two-sided. Results with a P-value of 0.05 or less were considered significant. Mean values, s.d., s.e.m. and statistics were calculated with Excel 2013 (Microsoft software). No criteria of inclusion or exclusion of data were used in this study.

Example 1 Chemical Synthesis of the Present Sulfated Octasaccharides

The present octasaccharides HS1-HS8 and HS9-HS16 were respectively synthesized in accordance with steps as described in schemes I and II. In general, the sugar backbones were assembled in a convergent manner using disaccharide and tetrasaccharide building blocks with thiotolyl functionality acting as leaving group. The protecting groups employed are according to the pattern used recently for heparin and heparosan synthesis (Hu et al., 2011 Nat. Chem. 3, 557-563; Zulueta et al., 2012 J. Am. Chem. Soc. 134, 8988-8995). With fully protected skeletons, functional group transformations were carried out in a divergent manner (Hu et al., 2012 J. Am. Che. Soc. 134, 20722-20727.) to afford differentially sulfonated final products with an aminopentyl aglycon moiety.

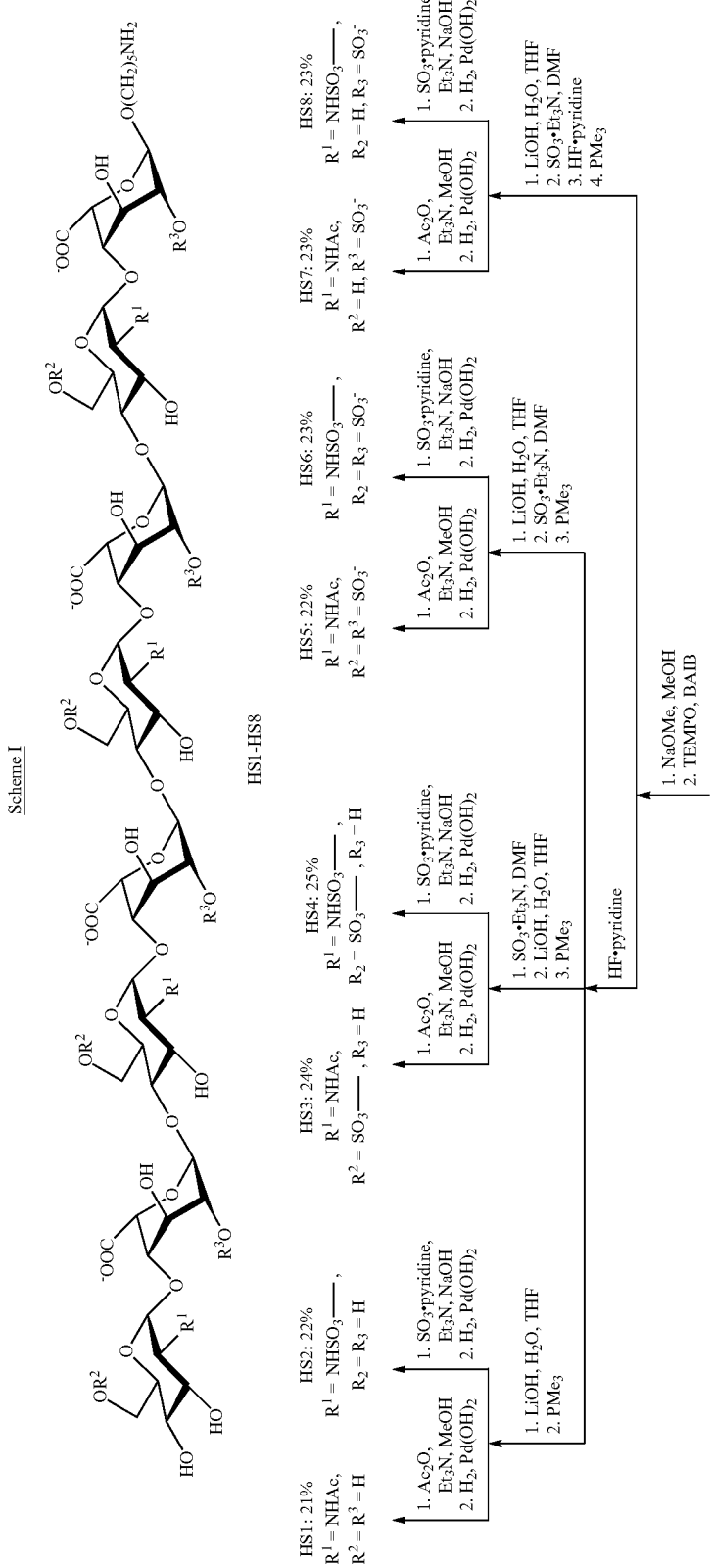

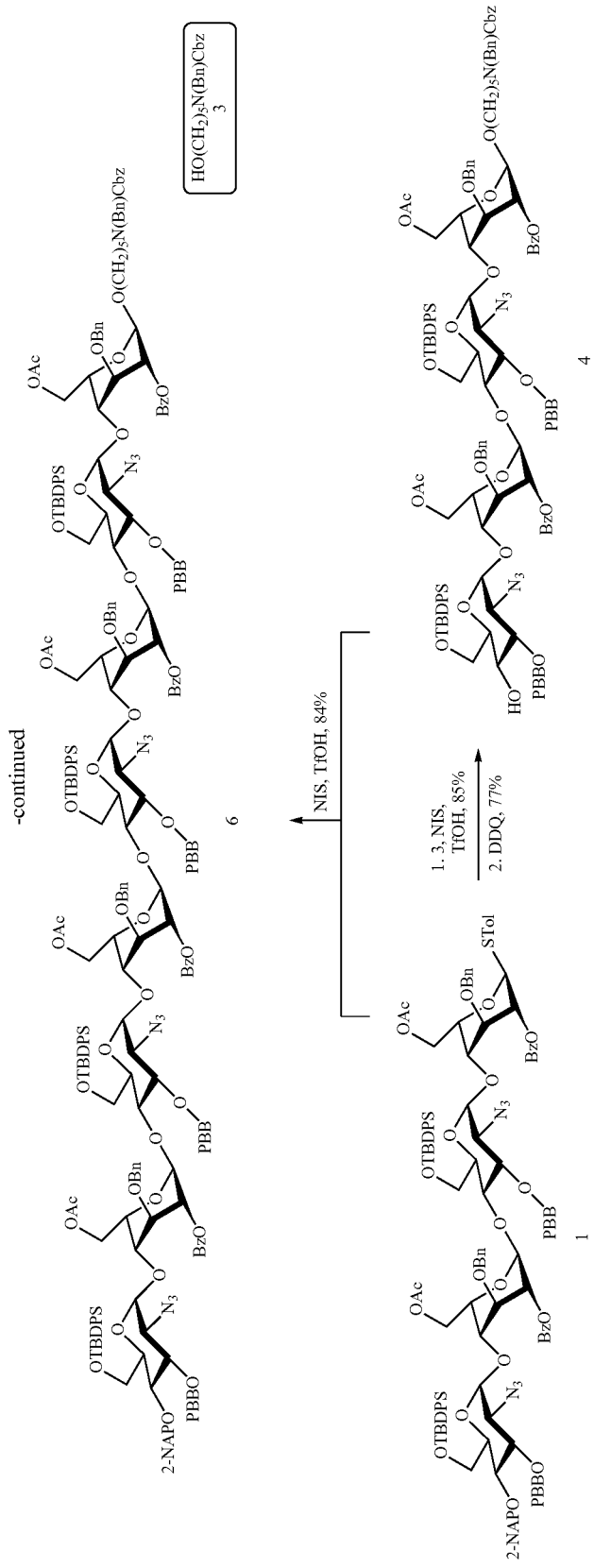

Scheme II
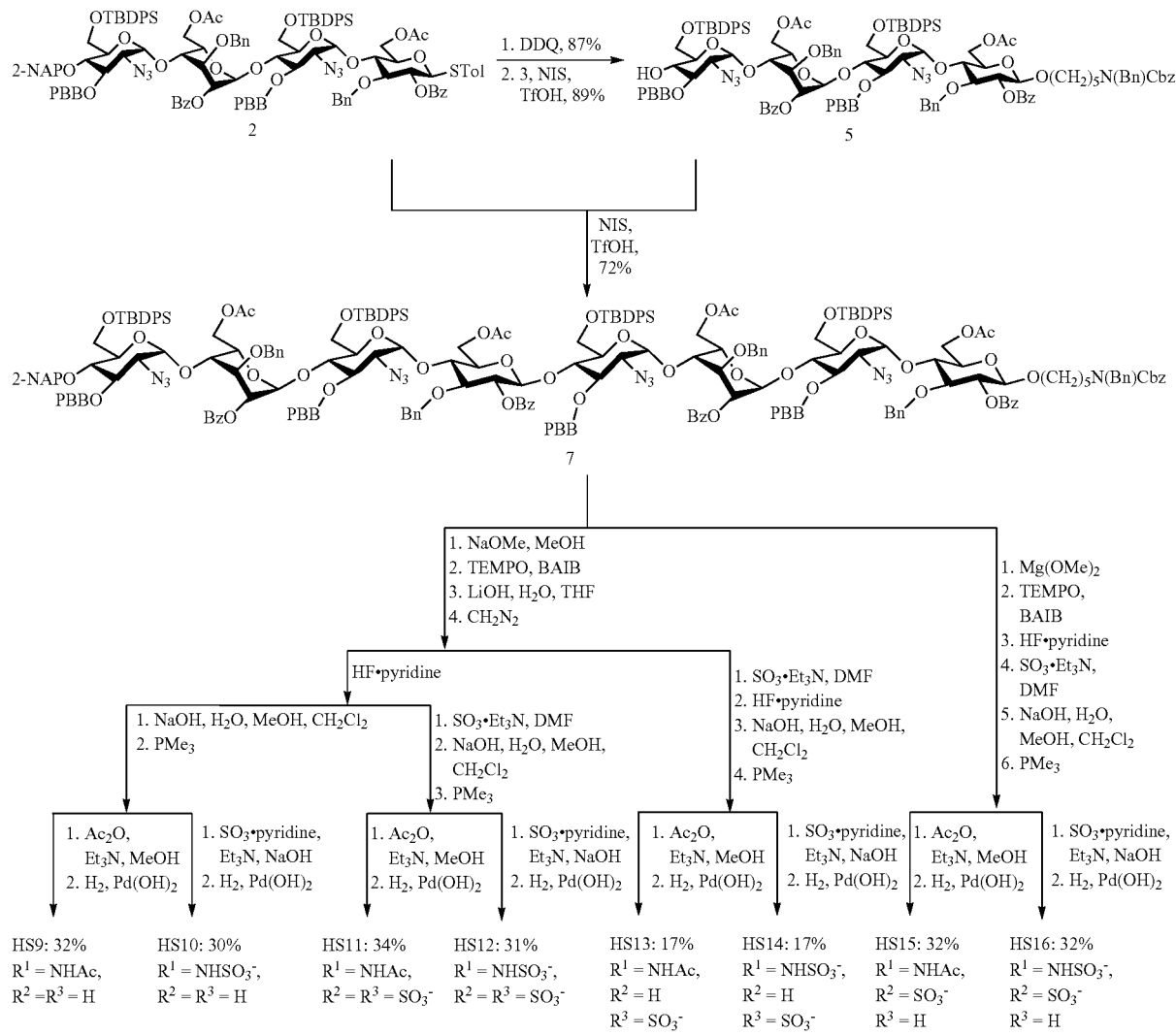
The chemical data of HS1 to HS 16 are provided bellowed.
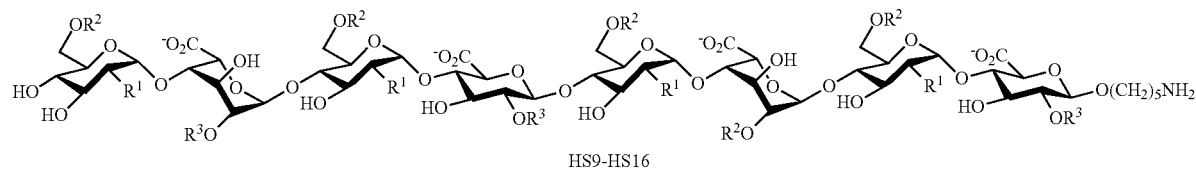
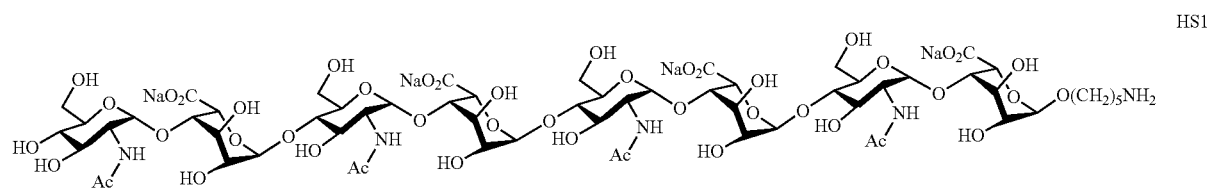

5-Aminopentyl (2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-α-L-idopyranosiduronate (HS1). $^1$H NMR (600 MHz, D$_2$O): δ 5.12-5.06 (m, 4H), 4.84-4.82 (m, 1H), 4.79-4.76 (m, 2H), 4.67-4.63 (m, 3H), 4.42 (d, J=2.8 Hz, 1H), 4.02-3.93 (m, 4H), 3.90-3.83 (m, 5H), 3.83-3.71 (m, 15H), 3.71-3.62 (m, 8H), 3.62-3.53 (m, 4H), 3.53-3.49 (m, 1H), 3.38 (t, J=9.5 Hz, 1H), 2.90 (t, J=7.6 Hz, 2H), 1.94 (s, 3H, Ac), 1.93 (s, 6H, Ac×2), 1.92 (s, 3H, Ac), 3H, Ac), 2.03 (s, 3H, Ac), 1.73-1.65 (m, 4H), 1.52-1.43 (m, 2H); $^{13}$C NMR (150 MHz, D$_2$O): δ 176.0 (C), 175.9 (C), 175.82 (C), 175.77 (C), 175.3 (C), 175.24 (C), 175.20 (C), 103.3 (CH), 103.2 (CH), 102.8 (C), 102.7 (CH), 97.95 (CH), 95.4 (CH), 95.3 (CH), 79.1 (CH), 78.1 (CH), 77.91 (CH), 77.87 (CH), 77.7 (CH), 77.5 (CH), 77.3 (CH), 77.19 (CH), 77.17 (CH), 75.6 (CH), 75.3 (CH), 74.5 (CH), 74.4 (CH), 72.9 (CH), 72.1 (CH), 71.7 (CH), 71.03 (CH$_2$), 71.00 (CH), 70.95 (CH), 70.9 (CH), 70.8 (CH), 70.7 (CH), 70.6 (CH), 70.5 (CH), 70.4 (CH), 61.2 (CH$_2$), 60.7 (CH$_2$), 60.6 (CH$_2$), 60.4 (CH$_2$), 54.8 (CH), 54.5 (CH), 54.1 (CH), 40.4 (CH$_2$), 29.1 (CH$_2$), 27.3 (CH$_2$), 22.9 (CH$_2$), 22.9 (CH$_3$); HRMS (ESI): m/z calcd for C$_{61}$H$_{94}$N$_5$Na$_5$O$_{45}$ ([M+5Na−3H]$^{2+}$): 865.7355, found: 865.7357.

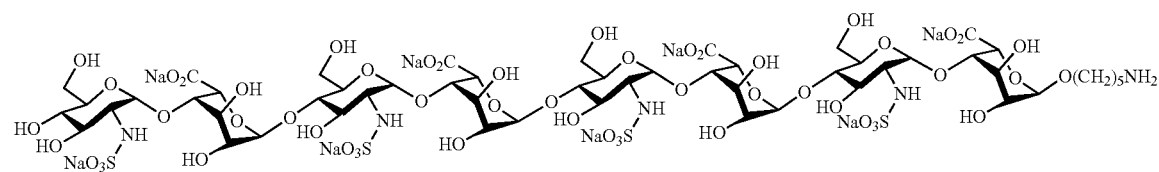

HS2

1.63-1.54 (m, 4H, CH$_2$ linker), 1.40-1.32 (m, 2H, CH$_2$ linker); $^{13}$C NMR (150 MHz, D$_2$O): δ 175.0 (C), 174.9 (C), 174.8 (C), 174.3 (C), 174.28 (C), 174.2 (C), 101.6 (CH), 100.7 (CH), 94.4 (CH), 94.3 (CH), 76.6 (CH), 76.5 (CH), 76.4 (CH), 74.5 (CH), 74.4 (CH), 74.3 (CH), 73.9 (CH), 71.9 (CH), 71.1 (CH), 71.05 (CH), 71.0 (CH), 69.9 (CH), 69.8 (CH), 69.7 (CH), 69.6 (CH), 69.4 (CH), 69.3 (CH), 68.8 (CH), 68.6 (CH), 68.0 (CH$_2$), 60.1 (CH$_2$), 60.0 (CH$_2$), 53.6 (CH), 53.5 (CH), 39.3 (CH$_2$), 28.0 (CH$_2$), 26.2 (CH$_2$), 22.2 (CH$_2$), 21.8 (CH$_3$); HRMS (ESI): m/z calcd for C$_{61}$H$_{95}$N$_5$O$_{45}$ ([M−2H]$^{2-}$) 808.7650, found: 808.7641.

5-Aminopentyl (2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-α-L-idopyranosiduronyl-(1→4)-(2-deoxy-2-sulfamido-α-D-glucopy-

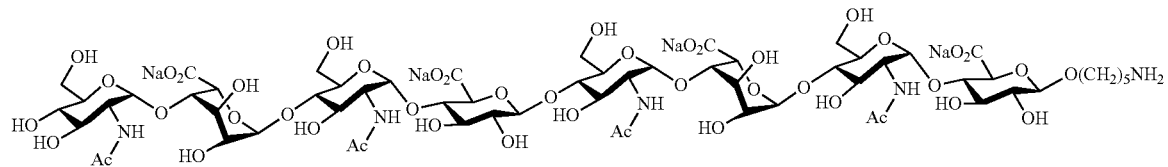

HS9

5-Aminopentyl (2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-β-D-glucopyranosiduronyl-(1→4)-(2-acetamido-2-deoxy-α-D-glucopyranosyl)-(1→4)-α-L-idopyranosiduronyl-(1→4)-(2-acetamido-2-deoxy-α-D-glucopyranosyl)-(1→4)-β-D-glucopyranosiduronate (HS9). $^1$H NMR (600 MHz, D$_2$O): δ 5.40 (d, J=3.8 Hz, 1H), 5.38 (d, J=3.8 Hz, 1H), 5.20 (d, J=3.7 Hz, 1H), 5.19 (d, J=3.7 Hz, 1H), 4.94 (d, J=3.7 Hz, 1H), 4.93 (d, J=3.9 Hz, 1H), 4.75 (d, J=3.1 Hz, 1H), 4.74 (d, J=2.9 Hz, 1H), 4.51 (d, J=7.9 Hz, 1H), 4.46 (d, J=8.0 Hz, 1H), 4.10 (t, J=6.8 Hz, 1H), 4.08 (t, J=6.6 Hz, 1H), 3.97-3.95 (m, 1H), 3.95-3.91 (m, 5H), 3.90-3.87 (m, 5H), 3.86-3.83 (m, 7H), 3.83-3.79 (m, 4H), 3.79-3.77 (m, 2H), 3.77-3.76 (m, 2H), 3.76-3.74 (m, 2H), 3.74-3.71 (m, 3H), 3.71-3.69 (m, 4H), 3.69-3.66 (m, 1H), 3.49 (t, J=9.4 Hz, 1H), 3.38 (t, J=8.6 Hz, 1H), 3.31 (t, J=8.6 Hz, 1H), 3.01 (t, J=7.5 Hz, 1H), 2.06 (s, 6H, Ac×2), 2.04 (s, ranosyl)-(1→4)-α-L-idopyranosiduronate (HS2). $^1$H NMR (600 MHz, D$_2$O): δ 5.41-5.35 (m, 4H), 4.98-4.94 (m, 2H), 4.92-4.89 (m, 2H), 4.51 (d, J=1.9 Hz, 1H), 4.16-4.02 (m, 8H), 3.92-3.59 (m, 27H), 3.47 (t, J=9.4 Hz, 1H), 3.28-3.19 (m, 4H), 3.00 (t, J=7.4 Hz, 2H), 1.72-1.63 (m, 2H), 1.48-1.43 (m, 2H); $^{13}$C NMR (150 MHz, D$_2$O): δ 175.2 (C), 101.6 (CH), 100.7 (CH), 95.64 (CH), 95.6 (CH), 95.5 (CH), 95.4 (CH), 77.1 (CH), 77.0 (CH), 76.9 (CH), 74.9 (CH), 74.8 (CH), 74.7 (CH), 71.7 (CH), 71.3 (CH), 71.0 (CH), 70.9 (CH), 69.8 (CH), 69.73 (CH), 69.7 (CH), 69.3 (CH), 69.1 (CH), 69.0 (CH), 68.8 (CH), 68.5 (CH), 68.4 (CH), 68.2 (CH), 68.1 (CH$_2$), 60.2 (CH$_2$), 59.7 (CH$_2$), 58.0 (CH), 57.8 (CH), 39.4 (CH$_2$), 28.0 (CH$_2$), 26.2 (CH$_2$), 22.2 (CH$_2$); HRMS (ESI): m/z calcd for C$_{53}$H$_{86}$N$_5$O$_{53}$S$_4$Na$_3$ ([M+3Na−6H]$^{3-}$) 611.4177, found: 611.4167.

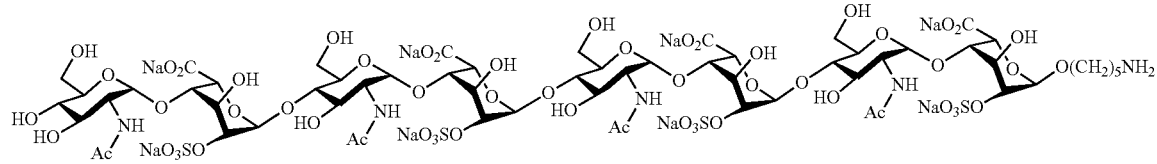

HS7

5-Aminopentyl (2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-2-O-sulfonato-α-L-idopyranosiduronate (HS7). $^1$H NMR (600 MHz, D$_2$O): δ 5.17 (bs, 4H), 5.11-5.08 (m, 4H), 4.90 (d, J=10.1 Hz, 2H), 4.54 (d, J=1.9 Hz, 1H), 4.32 (bs, 3H), 4.30-4.25 (m, 4H), 4.21 (bs, 1H), 4.03-3.96 (m, 9H), 3.90-3.83 (m, 9H), 3.82-3.76 (m, 4H), 3.75-3.67 (m, 8H), 3.45 (t, J=9.3 Hz, 1H), 2.99 (t, J=7.5 Hz, 2H), 2.05 (s, 6H, Ac×2), 2.04 (s, 6H, Ac×2), 1.70-1.61 (m, 4H, CH$_2$ linker), 1.50-1.40 (m, 2H, CH$_2$ linker); $^{13}$C NMR (150 MHz, D$_2$O): δ 175.8 (C), 175.2 (C), 174.8 (C), 174.7 (C), 99.3 (CH), 99.2 (CH), 98.6 (CH), 93.5 (CH), 93.4 (CH), 93.3 (CH), 77.2 (CH), 74.1 (CH), 73.3 (CH), 73.2 (CH), 73.1 (CH), 71.9 (CH), 71.3 (CH), 71.2 (CH), 70.7 (CH), 70.4 (CH), 70.2 (CH), 69.9 (CH), 69.8 (CH), 69.7 (CH), 68.1 (CH$_2$), 67.4 (CH), 67.3 (CH), 67.2 (CH), 64.0 (CH), 63.4 (CH), 63.3 (CH), 63.1 (CH), 60.2 (CH$_2$), 59.7 (CH$_2$), 39.4 (CH$_2$), 27.8 (CH$_2$), 26.2 (CH$_2$), 22.24 (CH$_3$), 22.2 (CH$_3$), 22.1 (CH$_3$); HRMS (ESI): m/z calcd for C$_{61}$H$_{94}$N$_5$O$_{57}$S$_4$ ([M−3H]$^{3-}$) 645.4498, found 645.4489.

idopyranosiduronyl-(1→4)-(2-deoxy-2-sulfamido-α-D-glucopyranosyl)-(1→4)-β-D-glucopyranosiduronate (HS10). $^1$H NMR (600 MHz, D$_2$O): δ 5.62 (d, J=3.7 Hz, 1H), 5.61 (d, J=3.6 Hz, 1H), 5.41 (d, J=3.4 Hz, 1H), 5.39 (d, J=3.4 Hz, 1H), 4.98 (bs, 1H), 4.96 (d, J=2.8 Hz, 1H), 4.55 (d, J=7.9 Hz, 1H), 4.50 (d, J=8.0 Hz, 1H), 4.14-4.07 (m, 4H), 3.94-3.88 (m, 4H), 3.88-3.84 (m, 6H), 3.84-3.81 (m, 7H), 3.81-3.78 (m, 4H), 3.76-3.74 (m, 3H), 3.74-3.70 (m, 4H), 3.68-3.63 (m, 3H), 3.48 (t, J=9.5 Hz, 1H), 3.43 (t, J=8.6 Hz, 1H), 3.36 (t, J=8.6 Hz, 1H), 3.31-3.25 (m, 3H), 3.23 (dd, J=10.3, 3.6 Hz, 1H), 3.02 (t, J=7.5 Hz, 2H), 1.75-1.65 (m, 4H), 1.53-1.43 (m, 2H); $^{13}$C NMR (150 MHz, D$_2$O): δ 176.3 (C), 176.1 (C), 176.0 (C), 103.3 (CH), 103.2 (CH), 102.8 (CH), 102.7 (CH), 98.5 (CH), 98.4 (CH), 96.5 (CH), 96.4 (CH), 78.9 (CH), 78.3 (CH), 78.11 (CH), 78.06 (CH), 77.94 (CH), 77.89 (CH), 77.6 (CH), 77.5 (CH), 76.0 (CH), 75.9 (CH), 73.81 (CH), 73.76 (CH), 72.7 (CH), 72.4 (CH), 71.94 (CH), 71.91 (C), 71.6 (CH), 71.1 (CH$_2$), 70.9 (CH), 70.84 (CH), 70.80 (CH), 70.5 (CH), 70.33 (CH), 70.28 (CH), 70.0 (CH), 69.6 (CH), 61.4 (CH$_2$), 60.81 (CH$_2$), 60.79 (CH$_2$), 60.5 (CH$_2$), 59.3 (CH), 59.0 (CH), 58.6 (CH), 40.5 (CH$_2$), 29.2 (CH$_2$), 27.3 (CH$_2$), 23.0 (CH$_2$); HRMS (ESI): m/z calcd for C$_{53}$H$_{81}$N$_5$Na$_8$O$_{53}$S$_4$ ([M+3Na−6H]$^{3-}$): 611.4177, found: 611.4176; calcd for C$_{53}$H$_{81}$N$_5$Na$_8$O$_{53}$S$_4$ ([M+4Na−7H]$^{3-}$): 618.7449, found: 618.7449.

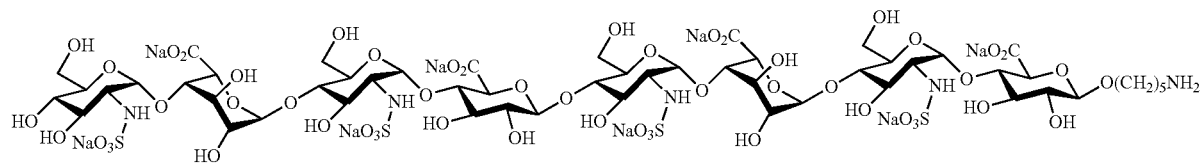

HS10

5-Aminopentyl (2-deoxy-2-sulfamido-α-D-glucopyranosyl)-(1→4)-α-L-idopyranosiduronyl-(1→4)-(2-deoxy-2-sulfamido-α-D-glucopyranosyl)-(1→4)-β-D-glucopyranosiduronyl-(1→4)-(2-deoxy-2-sulfamido-α-D-glucopyranosyl)-(1→4)-α-L-

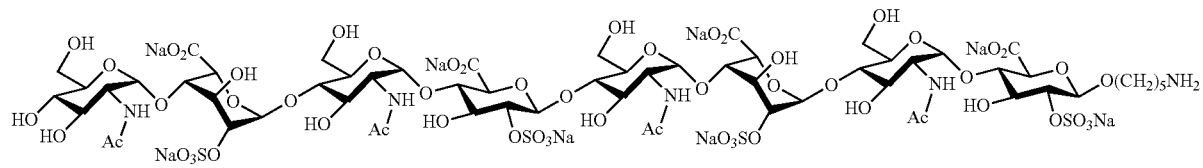

HS13

5-Aminopentyl (2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-(2-O-sulfonato-β-D-glucopyranosiduronyl-(1→4)-(2-acetamido-2-deoxy-α-D-glucopyranosyl)-(1→4)-(2-O-sulfonato-α-L-idopyranosiduronyl)-(1→4)-(2-acetamido-2-deoxy-α-D-glucopyranosyl)-(1→4)-2-O-sulfonato-f-D-glucopyranosiduronate (HS13). $^1$H NMR (600 MHz, D$_2$O): δ 5.39 (d, J=3.6 Hz, 1H), 5.38 (d, J=3.4 Hz, 1H), 5.23-5.20 (m, 2H), 5.14-5.12 (m, 2H), 4.92 (d, J=1.6 Hz, 1H), 4.89 (s, 1H), 4.73 (d, J=7.7 Hz, 1H), 4.63 (d, J=7.9 Hz, 1H), 4.35 (s, 1H), 4.34 (s, 1H), 4.32 (s, 1H), 4.28 (s, 1H), 4.16 (t, J=8.3 Hz, 1H), 4.10 (t, J=8.7 Hz, 1H), 4.06-4.00 (m, 4H), 4.00-3.97 (m, 2H), 3.95-3.90 (m, 5H), 3.88-3.85 (m, 10H), 3.84-3.80 (m, 6H), 3.78-3.66 (m, 6H), 3.48 (t, J=9.3 Hz, 1H), 3.03 (t, J=7.4 Hz, 2H), 2.09 (bs, 3H, Ac), 2.08 (bs, 3H, Ac), 2.07 (bs, 3H, Ac), 2.06 (bs, 3H, Ac), 1.74-1.65 (m, 4H, δ 5.43-5.38 (m, 2H), 5.21-5.18 (m, 2H), 5.01-4.99 (m, 2H), 4.62-4.58 (m, 2H), 4.49-4.46 (m, 2H), 4.39-4.36 (m, 4H), 4.25-4.22 (m, 3H), 4.12-4.10 (m, 3H), 4.02-3.98 (m, 5H), 3.99-3.96 (m, 2H), 3.93-3.91 (m, 2H), 3.85-3.82 (m, 3H), 3.80-3.73 (m, 14H), 3.61-3.57 (m, 2H), 3.39-3.36 (m, 2H), 3.35-3.31 (m, 1H), 3.04-3.00 (m, 2H), 2.07 (bs, 3H, Ac), 2.06 (bs, 3H, Ac), 2.04 (bs, 3H, Ac), 2.03 (bs, 3H, Ac), 1.71-1.67 (m, 4H, CH$_2$ linker), 1.52-1.46 (m, 2H, CH$_2$ linker); $^{13}$C NMR (150 MHz, D$_2$O): δ 176.1 (C), 176.02 (C), 175.99 (C), 175.42 (C), 175.37 (C), 175.32 (C), 175.28 (C), 103.3 (CH), 103.09 (CH), 103.06 (CH), 103.03 (CH), 103.0 (CH), 102.9 (CH), 98.1 (CH), 95.5 (CH), 83.1 (CH), 80.9 (CH), 78.4 (CH), 77.9 (CH), 77.8 (CH), 77.7 (CH), 77.6 (CH), 77.5 (CH), 77.3 (CH), 76.2 (CH), 75.2 (CH), 74.62 (CH), 74.57 (CH), 74.1 (CH), 73.0 (CH), 72.2 (CH), 71.2 (CH), 71.1 (CH$_2$), 70.7 (CH), 70.6 (CH), 70.5 (CH), 70.4 (CH), 70.3 (CH), 70.2 (CH), 70.1 (CH), 70.0 (CH), 67.4 (CH$_2$), 67.2 (CH$_2$), 66.9 (CH$_2$), 54.8 (CH), 54.5 (CH), 54.1 (CH), 40.5 (CH$_2$), 29.2 (CH$_2$), 27.3 (CH$_2$), 23.0 (CH$_3$).

HS3

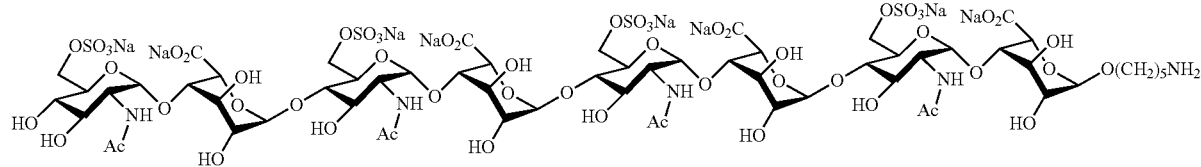

CH$_2$ linker), 1.56-1.48 (m, 2H, CH$_2$ linker); $^{13}$C NMR (150 MHz, D$_2$O): δ 176.8 (C), 176.4 (C), 175.9 (C), 175.8 (C), 175.7 (C), 175.6 (C), 175.4 (C), 175.3 (C), 101.7 (CH), 101.6 (CH), 100.4 (CH), 100.3 (CH), 98.3 (CH), 98.2 (CH), 94.70 (CH), 94.65 (CH), 81.6 (CH), 81.3 (CH), 80.7 (CH), 78.4 (CH), 77.7 (CH), 77.6 (CH), 77.4 (CH), 77.2 (CH), 76.6 (CH), 76.4 (CH), 74.8 (CH), 74.4 (CH), 73.0 (CH), 72.4 (CH), 72.34 (CH), 72.30 (CH), 71.8 (CH), 71.5 (CH), 71.1 (CH$_2$), 70.9 (CH), 70.6 (CH), 70.5 (CH), 68.6 (CH), 68.5 (CH), 65.1 (CH), 64.4 (CH), 61.4 (CH$_2$), 60.7 (CH$_2$), 60.5 (CH$_2$), 55.1 (CH), 54.5 (CH), 54.1 (CH), 40.5 (CH$_2$), 29.0 (CH$_2$), 27.3 (CH$_2$), 23.3 (CH$_3$), 23.0 (CH$_2$), 22.9 (CH$_3$); HRMS (ESI): m/z calcd for C$_{61}$H$_{91}$N$_5$O$_{57}$S$_4$Na$_8$ ([M+8Na−6H]$^{2+}$): 1058.6221, found: 1058.6226.

5-Aminopentyl (2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-L-idopyranosiduronate (HS3). $^1$H NMR (600 MHz, D$_2$O): δ 5.23-5.10 (m, 7H), 5.03-4.93 (m, 3H), 4.33-4.20 (m, 12H), 4.16-3.96 (m, 11H), 3.95-3.84 (m, 6H), 3.83-3.66 (m, 10H), 3.63-3.58 (m, 2H), 3.10-3.00 (m, 1H), 2.08 (bs, 6H, Ac), 2.04 (bs, 3H, Ac), 2.03 (bs, 3H, Ac), 1.80-1.65 (m, 4H, CH$_2$

HS15

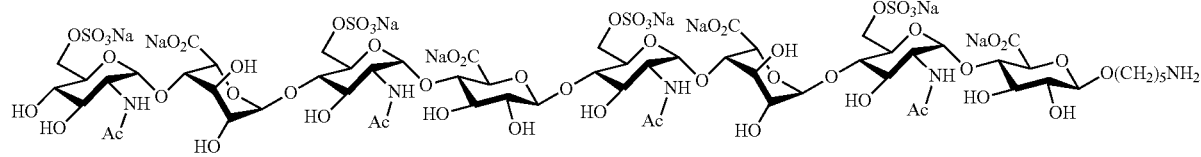

5-Aminopentyl (2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-glucopyranosyl)-(1→4)-α-D-glucopyranosiduronyl-(1→4)-(2-acetamido-2-deoxy-6-O-sulfonato-α-D-glucopyranosyl)-(1→4)-α-L-idopyranosiduronyl-(1→4)-(2-acetamido-2-deoxy-6-O-sulfonato-α-D-gluco pyranosyl)-(1→4)-β-D-glucopyranosiduronate (HS15). $^1$H NMR (600 MHz, D$_2$O):

linker), 1.52-1.46 (m, 2H, CH$_2$ linker); $^{13}$C NMR (150 MHz, D$_2$O): δ 175.5 (C), 175.3 (C), 175.2 (C), 175.0 (C), 174.8 (C), 174.4 (C), 102.0 (CH), 101.8 (CH), 100.8 (CH), 99.2 (CH), 94.4 (CH), 93.7 (CH), 74.0 (CH), 71.2 (CH), 71.0 (CH), 70.7 (CH), 70.1 (CH), 70.0 (CH), 69.8 (CH), 69.4 (CH), 69.3 (CH), 69.2 (CH), 69.0 (CH), 68.6 (CH), 68.1 (CH), 66.4 (CH), 66.2 (CH), 66.1 (CH$_2$), 53.6 (CH), 53.4 (CH), 53.2 (CH), 53.1 (CH), 39.4 (CH$_2$), 28.0 (CH$_2$), 26.1 (CH$_2$), 22.2 (CH$_3$); HRMS (MALDI): m/z calcd for C$_{61}$H$_{94}$N$_5$O$_{57}$S$_4$ ([M−3H]$^{3-}$): 645.4498, found: 645.4493.

HS5

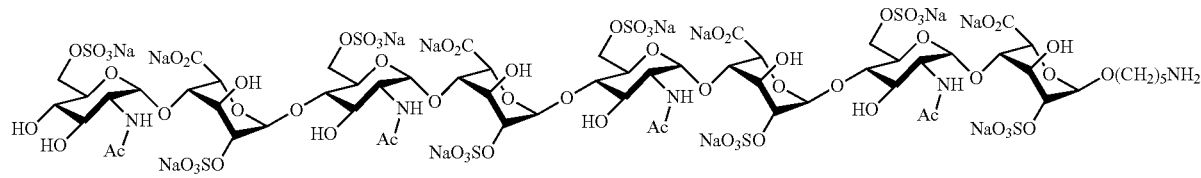

5-Aminopentyl (2-acetamido-2-deoxy-6-O-sulfonato-α-D-glucopyrano-syl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-2-O-sulfonato-α-L-idopyranosiduronate (HS5). $^1$H NMR (600 MHz, D$_2$O): δ 5.24-2.18 (m 5H), 5.18-5.08 (m, 5H), 5.04-4.89 (m, 2H), 4.35-4.20 (m, 13H), 4.15-3.93 (m, 9H), 3.94-3.79 (m, 4H), 3.79-3.59 (m, 10H), 3.56 (t, J=9.7 Hz, 1H), 3.00 (t, J=7.2 Hz, 2H), 2.08 (s, 3H, Ac), 2.06 (s, 3H, Ac), 2.01 (s, 6H, Ac×2), 1.73-1.59 (m, 4H), 1.52-1.38 (m, 2H); $^{13}$C NMR (150 MHz, D$_2$O): δ 174.8 (C), 174.4 (C), 174.3 (C), 172.7 (C), 101.8 (CH), 100.9 (CH), 99.1 (CH), 99.0 (CH), 98.5 (CH), 95.3 (CH), 94.9 (CH), 76.3 (CH), 76.2 (CH), 73.7 (CH), 73.6 (CH), 71.0 (CH), 70.8 (CH), 70.6 (CH), 70.56 (CH), 69.7 (CH), 69.6 (CH), 68.9 (CH), 68.7 (CH), 68.6 (CH$_2$), 67.4 (CH), 67.3 (CH), 66.5 (CH), 66.3 (CH$_2$), 66.1 (CH$_2$), 53.4 (CH), 53.3 (CH), 53.1 (CH), 39.3 (CH$_2$), 27.9 (CH$_2$), 27.6 (CH$_2$), 26.4 (CH$_2$), 22.2 (CH$_2$), 22.1 (CH$_3$), 21.9 (CH$_3$), 21.8 (CH$_3$); HRMS (ESI): m/z calcd for C$_{61}$H$_{93}$N$_5$O$_{69}$S$_8$ ([M−4H]$^{4-}$): 563.7922, found: 563.7941.

sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-α-L-idopyranosiduronate (HS4). $^1$H NMR (600 MHz, D$_2$O): δ 5.38-5.33 (m, 4H), 5.02 (bs, 4H), 4.89 (bs, 2H), 4.51 (d, J=2.4 Hz, 1H), 4.40-4.33 (m, 4H), 4.25-4.17 (m, 4H), 4.16-4.10 (m, 4H), 4.10-4.05 (m, 4H), 4.05-3.93 (m, 5H), 3.88-3.83 (m, 1H), 3.82-3.73 (m, 7H), 3.70-3.65 (m, 5H), 3.58 (t, J=9.7 Hz, 1H), 3.30-3.20 (m, 4H), 3.00 (td, J=2.1, 7.5 Hz, 2H), 1.73-1.64 (m, 4H, CH$_2$ linker), 1.49-1.43 (m, 2H, CH$_2$ linker); $^{13}$C NMR (150 MHz, D$_2$O): δ 175.4 (C), 175.2 (C), 101.9 (CH), 100.7 (CH), 95.6 (CH), 95.58 (CH), 95.5 (CH), 77.6 (CH), 77.4 (CH), 77.3 (CH), 71.2 (CH), 69.9 (CH), 69.8 (CH), 69.0 (CH), 68.9 (CH), 68.6 (CH), 68.4 (CH), 68.3 (CH), 68.0 (CH$_2$), 67.8 (CH), 67.5 (CH), 66.4 (CH$_2$), 66.2 (CH$_2$), 57.8 (CH), 57.7 (CH), 39.4 (CH$_2$), 28.0 (CH$_2$), 26.2 (CH$_2$), 22.2 (CH$_2$); HRMS (ESI): m/z calcd for C$_{53}$H$_{78}$N$_5$O$_{65}$S$_8$Na$_8$ ([M+8Na−11H]$^{3-}$): 754.6633, found: 754.6641.

HS4

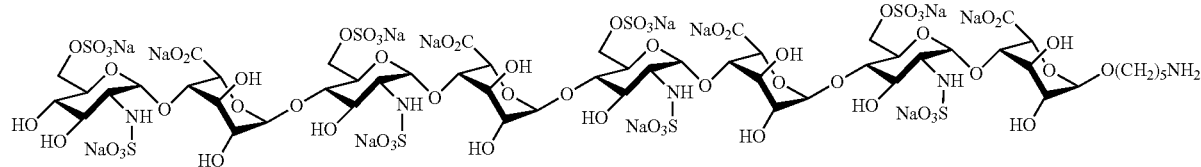

5-Aminopentyl (2-deoxy-2-sulfamido-6-O-sulfonato-α-D-glucopyranosyl)-(1→4)-α-L-idopyranosiduronyl-(1→4)-(2-deoxy-2-

HS14

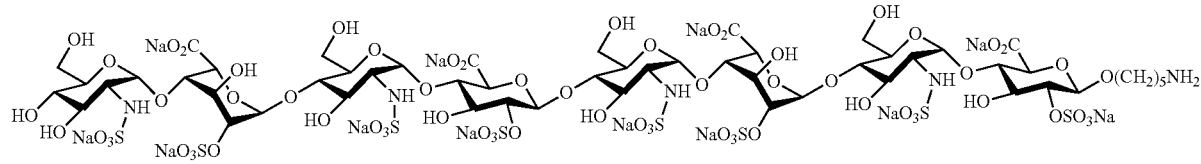

5-Aminopentyl (2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-(2-O-sulfonato-β-D-glucopyranosiduronyl-(1→4)-(2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-2-O-sulfonato-α-D-glucopyranosiduronate (HS14). $^1$H NMR (600 MHz, D$_2$O): δ 5.61 (d, J=3.7 Hz, 1H), 5.60 (d, J=3.5 Hz, 1H), 5.35-5.32 (m, 2H), 5.27 (bs, 2H), 4.89-4.87 (m, 1H), 4.72 (d, J=7.7 Hz, 1H), 4.64 (d, J=7.8 Hz, 1H), 4.37-4.34 (m, 2H), 4.29-4.25 (m, 2H), 4.18 (t, J=8.5 Hz, 1H), 4.12 (t, J=8.6 Hz, 1H), 4.08-4.04 (m, 3H), 4.01-3.98 (m, 2H), 3.90-3.84 (m, 12H), 3.83-3.80 (m, 4H), 3.77-3.73 (m, 2H), 3.73-3.70 (m, 3H), 3.70-3.65 (m, 5H), 3.48 (t, J=9.5 Hz, 1H), 3.28 (dd, J=10.6, 3.5 Hz, 1H), 3.27-3.22 (m, 3H), 3.02 (t, J=7.4 Hz, 1H), 1.72-1.63 (m, 4H, CH$_2$ linker), 1.57-1.46 (m, 2H, CH$_2$ linker); $^{13}$C NMR (150 MHz, D$_2$O): δ 176.5 (C), 176.2 (C), 175.9 (C), 175.6 (C), 101.8 (CH), 101.7 (CH), 100.2 (CH), 98.9 (CH), 98.3 (CH), 81.1 (CH), 80.7 (CH), 80.6 (CH), 78.4 (CH), 78.2 (CH), 78.1 (CH), 77.9 (CH), 77.5 (CH), 77.4 (CH), 76.6 (CH), 76.2 (CH), 75.9 (CH), 75.7 (CH), 72.7 (CH), 72.3 (CH), 72.2 (CH), 71.7 (CH), 71.10 (CH$_2$), 71.08 (CH), 70.93 (CH), 70.90 (CH), 70.4 (CH), 69.5 (CH), 69.3 (CH), 69.0 (CH), 68.8 (CH), 61.4 (CH$_2$), 60.8 (CH$_2$), 60.4 (CH$_2$), 59.4 (CH), 59.2 (CH), 58.9 (CH), 40.6 (CH$_2$), 29.1 (CH$_2$), 27.5 (CH$_2$), 23.0 (CH$_2$).

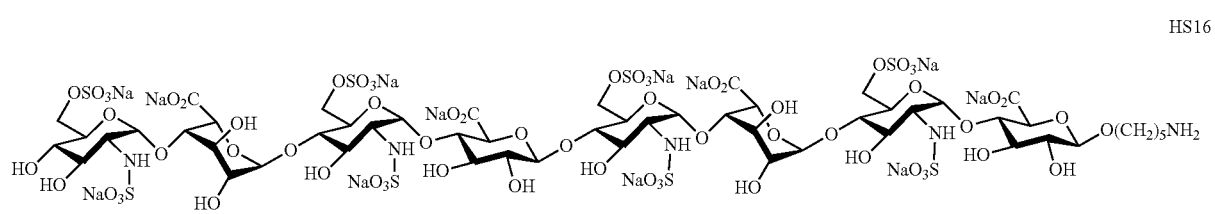

HS16

5-Aminopentyl (2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-β-D-glucopyranosiduronyl-(1→4)-(2-deoxy-2-sulfamido-6-O-sulfonato-α-D-glucopyranosyl)-(1→4)-α-L-idopyranosiduronyl-(1→4)-(2-deoxy-2-sulfamido-6-O-sulfonato-α-D-glucopyranosyl)-(1→4)-β-D-glucopyranosiduronate (HS16). $^1$H NMR (600 MHz, D$_2$O): δ 5.58 (bs, 1H), 5.38-5.32 (m, 2H), 5.04-4.99 (m, 2H), 4.76-4.72 (m, 2H), 4.62-4.58 (m, 2H), 4.46 (d, J=7.9 Hz, 1H), 4.38-4.30 (m, 2H), 4.21-4.17 (m, 3H), 4.12-4.10 (m, 2H), 4.03-4.00 (m, 1H), 3.95-3.92 (m, 1H), 3.88-3.83 (m, 2H), 3.81-3.67 (m, 13H), 3.66-3.62 (m, 2H), 3.58-3.54 (m, 2H), 3.53-3.49 (m, 1H), 3.40-3.36 (m, 1H), 3.34 (d, J=7.7 Hz, 1H), 3.32-3.30 (m, 2H), 3.29-3.24 (m, 3H), 3.21 (dd, J=10.3, 3.3 Hz, 1H), 2.99 (t, J=7.4 Hz, 1H), 1.71-1.60 (m, 4H, CH$_2$ linker), 1.50-1.40 (m, 2H, CH$_2$ linker); $^{13}$C NMR (150 MHz, D$_2$O): δ 176.51 (C), 176.47 (C), 176.1 (C), 176.0 (C), 103.2 (CH), 103.0 (CH), 102.94 (CH), 102.91 (CH), 98.7 (CH), 98.5 (CH), 96.6 (CH), 96.4 (CH), 78.7 (CH), 78.3 (CH), 78.2 (CH), 78.1 (CH), 77.8 (CH), 77.5 (CH), 77.4 (CH), 76.9 (CH), 76.7 (CH), 76.2 (CH), 75.6 (CH), 75.44 (CH), 75.40 (CH), 74.1 (CH), 73.9 (CH), 73.8 (CH), 73.0 (CH), 72.3 (CH), 71.02 (CH$_2$), 70.96 (CH), 70.9 (CH), 70.7 (CH), 70.1 (CH), 70.0 (CH), 69.9 (CH), 69.8 (CH), 69.65 (CH), 69.56 (CH), 69.5 (CH), 68.8 (CH), 67.4 (CH$_2$), 67.3 (CH$_2$), 66.9 (CH$_2$), 59.2 (CH), 58.8 (CH), 58.3 (CH), 40.5 (CH$_2$), 29.2 (CH$_2$), 27.3 (CH$_2$), 23.0 (CH$_2$); HRMS (ESI): m/z calcd for C$_{53}$H$_{79}$N$_5$O$_{65}$S$_8$Na$_6$ ([M+6Na−10H]$^{4−}$): 554.7546, found: 554.7562.

HS11

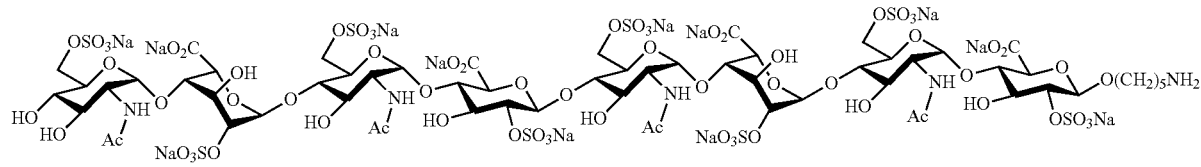

5-Aminopentyl (2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-(2-O-sulfonato-α-D-glucopyranosiduronyl)-(1→4)-(2-acetamido-2-deoxy-6-O-sulfonato-α-D-glucopyranosyl)-(1→4)-(2-O-sulfonato-α-L-idopyranosiduronyl)-(1→4)-(2-acetamido-2-deoxy-6-O-sulfonato-α-D-glucopyranosyl)-(1→4)-2-O-sulfonato-α-D-glucopyranosiduronate (HS11). $^1$H NMR (600 MHz, D$_2$O): δ 5.42 (s, 1H), 5.38 (s, 1H), 5.23 (s, 2H), 5.19 (s, 2H), 4.94 (s, 1H), 4.89 (s, 1H), 4.64 (d, J=7.7 Hz, 1H), 4.60 (d, J=10.6 Hz, 1H), 4.40-4.35 (m, 5H), 4.33 (bs, 1H), 4.29-4.25 (m, 5H), 4.18 (t, J=8.4 Hz, 1H), 4.13-4.07 (m, 4H), 4.07-4.00 (m, 6H), 3.98-3.91 (m, 5H), 3.89-3.81 (m, 9H), 3.77 (d, J=9.6 Hz, 1H), 3.75-3.70 (m, 2H), 3.59 (t, J=9.6 Hz, 1H), 3.04 (t, J=7.3 Hz, 2H), 2.09 (bs, 6H, CH$_3$×2), 2.08 (bs, 3H, Ac), 2.07 (bs, 3H, Ac), 1.75-1.66 (m, 4H, CH$_2$ linker), 1.56-1.49 (m, 2H, CH$_2$ linker); $^{13}$C NMR (150 MHz, D$_2$O): δ 176.4 (C), 176.1 (C), 175.8 (C), 175.7 (C), 175.4 (C), 175.3 (C), 101.5 (CH), 101.0 (CH), 100.1 (CH), 100.0 (CH), 98.3 (CH), 98.1 (CH), 95.2 (CH), 94.8 (CH), 81.6 (CH), 81.1 (CH), 78.9 (CH), 77.8 (CH), 77.6 (CH), 77.3 (CH), 77.1 (CH), 76.9 (CH), 76.5 (CH), 76.4 (CH), 75.4 (CH), 74.9 (CH), 73.4 (CH), 72.3 (CH), 72.1 (CH), 71.13 (CH), 71.11 (CH$_2$), 70.5 (CH), 70.4 (CH), 70.34 (CH), 70.30 (CH), 70.26 (CH), 70.1 (CH), 69.2 (CH), 68.9 (CH), 67.5 (CH$_2$), 67.3 (CH$_2$), 66.8 (CH$_2$), 66.3 (CH), 65.2 (CH), 54.7 (CH), 54.3 (CH), 54.0 (CH), 40.5 (CH$_2$), 29.0 (CH$_2$), 27.3 (CH$_2$), 23.3 (CH$_3$), 22.97 (CH$_2$), 22.95 (CH$_3$); HRMS (ESI): m/z calcd for C$_{61}$H$_{87}$N$_5$O$_{69}$S$_8$Na$_6$ ([M+6Na−10H]$^{4-}$): 596.7651, found: 596.7657.

HS8

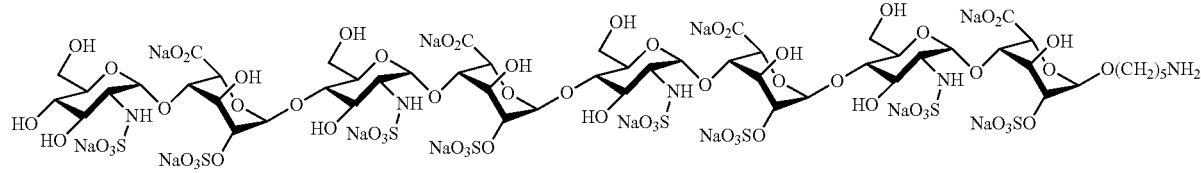

5-Aminopentyl (2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-(2-O-sulfonato-α-L-idopyranosiduronyl)-(1→4)-(2-deoxy-2-sulfamido-α-D-glucopyranosyl)-(1→4)-2-O-sulfonato-α-L-idopyranosiduronate (HS8). $^1$H NMR (600 MHz, D$_2$O): δ 5.40-5.27 (m, 7H), 5.10 (d, J=2.5 Hz, 1H), 4.93-4.90 (m, 1H), 4.87-4.85 (m, 1H), 4.89-4.87 (m, 1H), 4.48-4.47 (m, 1H), 4.38-4.31 (m, 4H), 4.27-4.20 (m, 4H), 4.19-4.17 (m, 1H), 4.11-4.00 (m, 5H), 3.91-3.80 (m, 12H), 3.78-3.64 (m, 11H), 3.45 (t, J=9.6 Hz, 1H), 3.26-3.20 (m, 4H), 2.99 (t, J=7.9 Hz, 1H), 1.71-1.59 (m, 4H, CH$_2$ linker), 1.50-1.39 (m, 2H, CH$_2$ linker); HRMS (ESI): m/z calcd for C$_{53}$H$_{84}$N$_5$O$_{65}$S$_8$ ([M−5H]$^{5-}$): 417.2238, found: 417.2224.

HS12

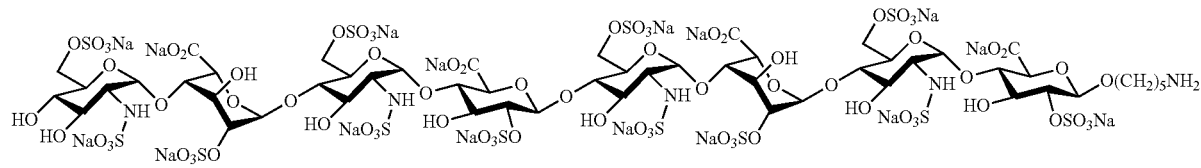

5-Aminopentyl (2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-β-D-glucopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-2-O-sulfonato-β-D-glucopyranosiduronate (HS12). $^1$H NMR (600 MHz, D$_2$O): δ 5.68 (d, J=3.6 Hz, 1H), 5.64 (d, J=3.6 Hz, 1H), 5.49-5.46 (m, 2H), 5.30 (bs, 2H), 4.98 (d, J=1.08 Hz, 1H), 4.94 (d, J=1.0 Hz, 1H), 4.66 (d, J=7.7 Hz, 1H), 4.60 (d, J=10.8 Hz, 1H), 4.44-4.38 (m, 5H), 4.38-4.34 (m, 2H), 4.33-4.28 (m, 2H), 4.26 (d, J=10.0 Hz, 2H), 4.24-4.20 (m, 3H), 4.16 (dd, J=8.70, 8.19 Hz, 1H), 4.10-4.06 (m, 2H), 4.05-3.98 (m, 6H), 3.98-3.97 (m, 1H), 3.97-3.92 (m, 4H), 3.92 (bs, 1H), 3.91-3.84 (m, 4H), 3.79 (t, J=9.7 Hz, 1H), 3.75-3.70 (m, 1H), 3.61 (t, J=9.7 Hz, 1H), 3.45 (dd, J=10.7, 3.7 Hz, 1H), 3.43-3.38 (m, 3H), 3.05 (t, J=7.4 Hz, 2H), 1.76-1.66 (m, 4H, CH$_2$ linker), 1.59-1.49 (m, 2H, CH$_2$ linker); $^{13}$C NMR (150 MHz, D$_2$O): δ 176.4 (C), 176.1 (C), 175.6 (C), 101.6 (CH), 101.0 (CH), 99.9 (CH), 99.6 (CH), 97.0 (CH), 96.7 (CH), 92.3 (CH), 92.2 (CH), 81.1 (CH), 80.7 (CH), 78.3 (CH), 78.0 (CH), 77.9 (CH), 77.2 (CH), 77.0 (CH), 76.9 (CH), 76.3 (CH), 76.1 (CH), 76.0 (CH), 74.0 (CH), 73.8 (CH), 71.8 (CH), 71.3 (CH), 71.1 (CH$_2$), 70.8 (CH), 70.7 (CH), 70.4 (CH), 69.8 (CH), 69.5 (CH), 69.3 (CH), 68.7 (CH), 68.3 (CH), 68.2 (CH), 67.14 (CH$_2$), 67.07 (CH$_2$), 66.5 (CH$_2$), 64.0 (CH), 63.6 (CH), 55.4 (CH), 55.2 (CH), 55.0 (CH), 40.5 (CH$_2$), 29.0 (CH$_2$), 27.2 (CH$_2$), 23.0 (CH$_2$).

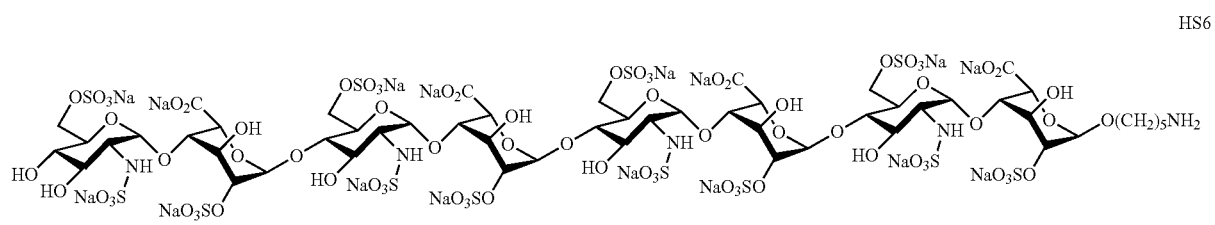

HS6

5-Aminopentyl (2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-(2-O-sulfonato-α-L-idopyranosiduronyl)-(1→4)-(2-deoxy-2-sulfamido-6-O-sulfonato-α-D-glucopyranosyl)-(1→4)-2-O-sulfonato-α-L-idopyranosiduronate (HS6). $^1$H NMR (600 MHz, D$_2$O): δ 5.43-5.36 (m 4H), 5.24-5.15 (m, 4H), 5.09-5.04 (m, 2H), 4.76-4.75 (m, 2H), 4.48-4.46 (m, 1H), 4.43-4.29 (m, 7H), 4.28-4.15 (m, 9H), 4.12-3.95 (m, 8H), 3.83-3.71 (m, 5H), 3.69-3.60 (m, 5H), 3.54 (t, J=9.4 Hz, 1H), 3.29-3.19 (m, 4H), 3.01-2.93 (m, 2H), 1.69-1.51 (m, 4H), 1.47-1.39 (m, 2H); $^{13}$C NMR (150 MHz, D$_2$O): δ 99.0 (CH), 97.7 (CH), 97.3 (CH), 97.2 (CH), 96.8 (CH), 76.4 (CH), 76.3 (CH), 76.2 (CH), 76.1 (CH), 76.0 (CH), 75.9 (CH), 75.8 (CH), 75.4 (CH), 68.9 (CH), 68.8 (CH), 68.6 (CH), 68.2 (CH$_2$), 66.4 (CH$_2$), 66.3 (CH$_2$), 57.9 (CH), 39.4 (CH$_2$), 27.8 (CH$_2$), 26.2 (CH$_2$), 22.2 (CH$_2$); HRMS (ESI): m/z calcd for C$_{53}$H$_{73}$N$_5$O$_{77}$Si$_2$Na$_4$H$_{12}$ ([M+4Na−9H]$^{5-}$): 498.7747, found: 498.7736.

Example 2 Capturing Cholangio-Cancerous Cells by Use of Magnetic Beads Pre-Coated with Sulfated Octasaccharides of Example 1

A microfluid system for capturing cancerous cells using magnetic beads pre-coated with the sulfated octasaccharides of Example 1 was constructed in accordance with procedures described in the "Materials and Methods" section.

In a pre-test, total of 8 cancer cell lines (i.e., MMNK-1, SNU-478, HuCCT-1, Huh-28, KKU-100, HepG2, BxPC3, and HCT8) were respectively loaded into the microsystem and incubated with the magnetic beads, then the captured cells were collected with a magnetic force, and finally loaded into a hemocytometer to calculate the capture rates. Results are summarized in Table 1.

TABLE 1

The capture rates (%) for various cell lines with HS 1 or HS 12 of Example 1

| | HS | | | | | | EpCAM (%) |
|---|---|---|---|---|---|---|---|
| | HS 12 (%) | | | HS 1 (%) | | | |
| | Concentration (μM) | | | | | | |
| Cell lines | 1 | 10 | 100 | 1 | 10 | 100 | |
| MMNK-1 | 55 ± 7 | 47 ± 20 | 16 ± 8 | 58 ± 11 | 52 ± 6 | 34 ± 5 | 58 ± 8 |
| SNU-478 | 20 ± 5 | 17 ± 7 | 16 ± 8 | 23 ± 13 | 20 ± 8 | 22 ± 7 | 74 ± 6 |
| HuCCT-1 | 5 ± 1 | 5 ± 2 | 4 ± 2 | 4 ± 1 | 6 ± 2 | 4 ± 1 | 67 ± 11 |
| Huh-28 | 66 ± 6 | 67 ± 3 | 73 ± 4 | 65 ± 20 | 70 ± 10 | 78 ± 14 | 58 ± 19 |
| KKU-100 | 42 ± 3 | 44 ± 2 | 41 ± 11 | 40 ± 10 | 46 ± 1 | 51 ± 2 | 51 ± 5 |
| HepG2 | 14 ± 1 | 11 ± 4 | 9 ± 6 | 12 ± 0 | 16 ± 6 | 10 ± 4 | 44 ± 7 |
| BxPC3 | 16 ± 6 | 11 ± 3 | 7 ± 3 | 15 ± 5 | 18 ± 4 | 13 ± 7 | 45 ± 6 |
| HCT8 | 16 ± 3 | 13 ± 0 | 9 ± 2 | 18 ± 5 | 14 ± 4 | 13 ± 3 | 22 ± 3 |

Among the eight cell lines, HS12 and HS 1 were highly specific to Huh28, a cholangiocarcinoma (CCA) cell lines. The highest capture rate of Huh28 captured by HS 12 and HS1 of 100 μM-coated beads were 73±4% and 78±14%, respectively, which were higher than that captured by the epithelial cell adhesion molecule (EpCAM)-coated beads (only 58±19%). Furthermore, HS 12 and HS1 were even more specific since the capture rates of the normal cells (MINK-1) and metastasized CCA cells (HuCCT-1) were relatively low. Therefore, HS 12 and HS1 may be promising as specific affinity reagents for detecting the presence of CCA cells.

Figure 2:
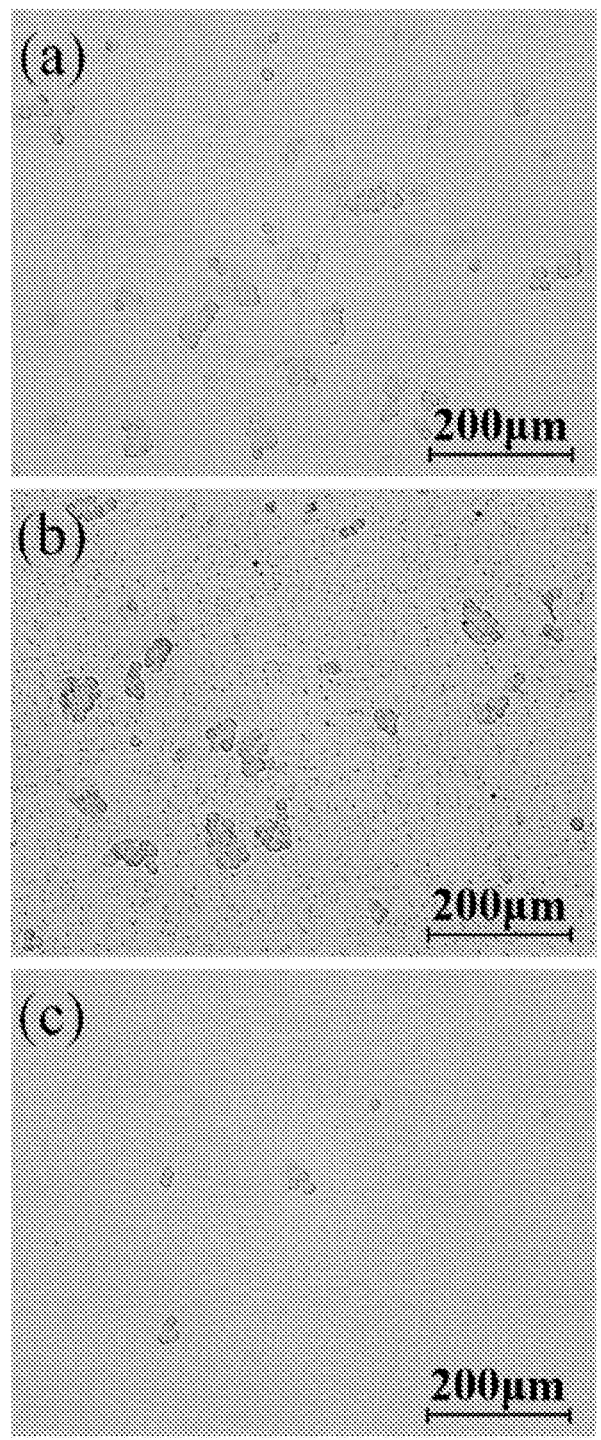
FIG. 2: Photographs depicting Huh-28 cells captured by HS1-coated beads. (a) un-captured Huh-28 cells, (b) Huh-28 cells captured by HS-1-coated beads after 30-min of incubation, and (c) supernatant collected from the magnetic beads-cell complex. All images were at 100× magnification.

FIG. 2 illustrates that the cancer cells, Huh-28, could be successfully captured by magnetic beads pre-coated with HS 1 of 100 μM. Huh-28 cells before being captured by magnetic beads are depicted in FIG. 2, panel a. After well mixing Huh-28 cells and beads for 30 mins, cells were surrounded by beads (FIG. 2, panel b). The supernatant collection through an isolation process by magnetic force after 30-min incubation is depicted in FIG. 2, panel c. Almost all of the Huh-28 cells were captured and isolated by magnetic beads, and only a few cells were observed in the supernatant. It indicates that most of the Huh-28 cells were captured.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A method of detecting cholangio-cancerous cells from a biological sample comprising: contacting the biological sample with a magnetic bead pre-coated with an octasaccharide of formula (I),

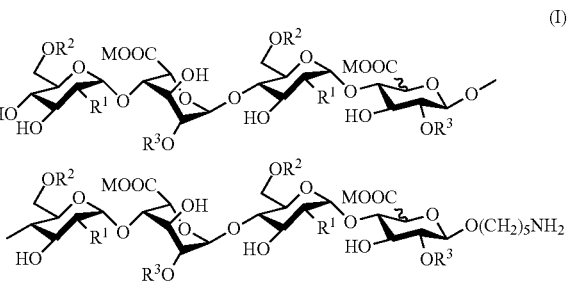

wherein,
$R^1$ is —NHSO$_3$M;
$R^2$ and $R^3$ are independently —SO$_3$M; and
M is a monovalent cation selected from the group consisting of sodium ion, potassium ion, lithium ion and ammonium ion; and
a binding between the magnetic bead and the biological sample indicates the detection of cholangio-cancerous cells in the biological sample.

2. The method of claim 1, wherein the octasaccharide of formula (I) is further coupled to a biotin.

3. The method of claim 1, wherein in the octasaccharide of formula (I), $R^1$ is —NHSO$_3$Na; and $R^2$ and $R^3$ are independently —SO$_3$Na.

4. The method of claim 1, wherein the biological sample is selected from the group consisting of blood, plasma, serum, urine, sputum, saliva, tissue sample, biopsy, and tissue lysate.

* * * * *